United States Patent [19]

Blanchard et al.

[11] Patent Number: 5,336,804
[45] Date of Patent: Aug. 9, 1994

[54] AMMOXIDATION OF SATURATED HYDROCARBONS

[75] Inventors: Gilbert Blanchard, Le Plessis Belleville; Gilbert Ferre, Livry Gargan, both of France

[73] Assignee: Rhone-Poulenc Chimie, Courbevoie, France

[21] Appl. No.: 14,757

[22] Filed: Feb. 8, 1993

[30] Foreign Application Priority Data

Feb. 6, 1992 [FR] France ................. 9201536

[51] Int. Cl.$^5$ ......................................... C07C 253/24
[52] U.S. Cl. ............................................ 558/319
[58] Field of Search .................................. 558/319

[56] References Cited

U.S. PATENT DOCUMENTS

| | | | |
|---|---|---|---|
| 3,365,482 | 1/1968 | Khooblar | 558/319 |
| 3,395,159 | 7/1968 | Levine | 558/319 |
| 3,433,823 | 3/1969 | McMahon | 558/319 |
| 3,670,009 | 6/1972 | Taylor | 558/319 |
| 3,678,090 | 7/1972 | Taylor | 558/319 |
| 3,686,267 | 8/1972 | Taylor | 558/319 |
| 3,746,737 | 7/1973 | Tullman | 558/319 |
| 3,833,638 | 9/1974 | Knox et al. | 558/319 |
| 3,927,007 | 12/1975 | Lussling et al. | 558/319 X |
| 4,309,361 | 1/1982 | Suresh et al. | 558/319 X |
| 4,760,159 | 7/1988 | Suresh et al. | 558/319 |
| 4,767,739 | 8/1988 | Glaeser et al. | 558/319 X |
| 4,783,545 | 11/1988 | Glaeser et al. | 558/319 |
| 4,801,568 | 1/1989 | Brazdil Jr., et al. | 558/319 X |
| 4,801,727 | 1/1989 | Glaeser et al. | 558/319 |
| 4,814,478 | 3/1989 | Glaeser et al. | 558/319 |
| 4,866,024 | 9/1989 | Brazdil, Jr. et al. | 558/319 X |
| 4,871,706 | 10/1989 | Brazdil, Jr. et al. | 502/209 X |
| 4,877,764 | 10/1989 | Glaeser et al. | 502/209 X |
| 4,883,896 | 11/1989 | Glaeser et al. | 558/319 |
| 4,888,438 | 12/1989 | Glaeser et al. | 558/319 |
| 5,008,427 | 4/1991 | Brazdil, Jr. et al. | 558/319 |

FOREIGN PATENT DOCUMENTS

| | | |
|---|---|---|
| 0282314 | 9/1988 | European Pat. Off. . |
| 0342777A3 | 11/1989 | European Pat. Off. . |
| 0344884A3 | 12/1989 | European Pat. Off. . |
| 2027238 | 9/1970 | France . |
| 2072334 | 9/1971 | France . |
| 2072399 | 9/1971 | France . |
| 2119492 | 8/1972 | France . |
| 2119493 | 8/1972 | France . |
| 1336135 | 11/1973 | United Kingdom . |
| 1336136 | 11/1973 | United Kingdom . |
| 1337759 | 11/1973 | United Kingdom . |

OTHER PUBLICATIONS

Kim, et al., Chemistry Letters, 1989, pp. 2173–2176.
J. Catal., 127(1), pp. 354–365, (1991), Azimov, A. B. et al, "Dehydrogenation mechanism for ammoxidation of alkylaromatic hydrocarbons".
Japanese Patent Abstract No. JP3058961, Published Mar. 14, 1991, Application No.JP890191317.

*Primary Examiner*—Joseph Paul Brust
*Attorney, Agent, or Firm*—Burns, Doane, Swecker & Mathis

[57] ABSTRACT

The alkanes, e.g., propane, are ammoxidized into admixtures containing $\alpha,\beta$-unsaturated nitriles, e.g., admixture of acrylonitrile and propylene, by reacting such alkane with ammonia and oxygen, in vapor phase, in the presence of a catalytically effective amount of a solid catalyst, at least one active catalytic phase of which having the empirical formula (I):

$$VSb_aBi_bO_x \qquad (I)$$

optionally also containing iron and/or gallium and/or indium, in which a is a whole or fractional number equal to or greater than 1, b is a whole or fractional number equal to or greater than 0.01, and x is a whole or fractional number provided by the oxidation number of the other elements of the at least one active catalytic phase.

21 Claims, 1 Drawing Sheet

AMMOXIDATION OF SATURATED HYDROCARBONS

BACKGROUND OF THE INVENTION

1. Field of the Invention

The present invention relates to the ammoxidation of saturated hydrocarbons, and, more especially, to the ammoxidation/conversion of alkanes into a mixture containing $\alpha,\beta$-unsaturated nitriles.

2. Description of the Prior Art

The ammoxidation of olefins and, in particular, of propylene, is well known to this art. However, although the saturated hydrocarbons, which are more widely available, are the more desirable starting materials from an economic standpoint, it is also well known to this art that these do not display comparable reactivity in this type of reaction to form, especially, $\alpha,\beta$-unsaturated nitriles.

One of the difficulties encountered in the ammoxidation of saturated hydrocarbons is the requirement for catalysts capable of dehydrogenating the saturated hydrocarbon under conditions which minimize or eliminate the combustion of the ammonia and/or that of the hydrocarbon, while at the same time ensuring a reasonable selectivity either for the $\alpha,\beta$-unsaturated nitrile (target compound), for example for acrylonitrile starting from propane, or for added value compounds (above-mentioned nitrile and olefin), for example, for acrylonitrile and propylene starting from propane.

U.S. Pat. No. 3,365,482, describes the ammoxidation, especially of isobutane into methacrylonitrile, on a molybdenum-based catalyst deposited onto eta-alumina, doped with antimony, at 508° C., beginning with a gaseous mixture containing isobutane, air, ammonia and steam (1.0/4.5/1.0/12.5); the selectivity for methacrylonitrile attains a value of 49% for a degree of conversion of the isobutane of 22%.

When the starting material is a gaseous mixture of propane/air/ammonia/steam (1.0/4.7/0.67/12.8), using the same catalyst and at 550° C., the selectivity for acrylonitrile decreases to 15% for a degree of conversion of the propane of 29%.

In *Chemistry Letters*, pp. 2173–2176 (1989), the ammoxidation of propane in the vapor phase is described, in the presence of multicomponent metal oxides containing molybdenum and bismuth and having a structure of the type of that of scheelite. It appears that, despite the relatively moderate temperatures used, the proportion of combustion products (CO, CO$_2$) is very high in all instances (at least 15%) and that certain catalytic compositions tested exhibit very little activity with respect to the desired reaction, while being used under conditions which are in the explosive region or very near the explosive region.

It is immediately apparent that the coproduction of large amounts of CO and CO$_2$ is undesirable on an industrial scale.

In addition, the use of reaction mixtures which are in the explosive region, compositionally, is even less desirable on an industrial scale, since the process is carried out in a stationary bed.

U.S. Pat. No. 4,760,159 describes a process for the ammoxidation of an alkane having from 3 to 5 carbon atoms into an $\alpha,\beta$-unsaturated nitrile having from 3 to 5 carbon atoms, by reaction in the gas phase with ammonia and oxygen, in the presence of a solid catalyst having the formula $Bi_aV_bL_lM_mT_tO_x$, in which Bi, V, M (which is selected from among Mo, W, Cr, Ge and Sb) and 0 are necessarily present.

From the various examples set forth in this '159 patent, it is seen that the best selectivities towards $\alpha,\beta$-unsaturated nitriles are obtained using catalysts containing vanadium, bismuth and molybdenum and, optionally, another cation such as chromium, potassium, zinc, cesium or antimony. The only example using a catalyst based on vanadium, bismuth and antimony, having the formula $BiV_{0.7}Sb_{0.50}O_x$ and deposited onto a silica/alumina mixture, in an amount of 50% by weight, produces yields of $\alpha,\beta$-unsaturated nitrile which are markedly lower than those attained using a catalyst containing molybdenum.

Additionally, this process also forms a not insignificant amount of the oxides of carbon (CO+CO$_2$).

SUMMARY OF THE INVENTION

Accordingly, a major object of the present invention is the provision of an improved process for the appreciably selective ammoxidation of alkanes into admixture of added value compounds containing an $\alpha,\beta$-unsaturated nitrile, in particular acrylonitrile, while reducing the losses in starting material, especially by reason of the formation of oxides of carbon.

Another object of this invention is the provision of an improved process for the ammoxidation of alkanes in the presence of a solid catalyst that is relatively simple to prepare and active in the absence of halogenated promoter and effective in respect of gas mixtures which are not necessarily in the explosive region.

Briefly, the present invention features a process for the ammoxidation of alkanes in the vapor phase in the presence of a solid catalyst comprising at least one active phase, said at least one active phase having the empirical formula (I):

$$VSb_aBi_bO_x \qquad (I)$$

in which a is a whole or fractional number equal to or greater than 1, b is a whole or fractional number equal to or greater than 0.01, and x is a whole or fractional number provided by the oxidation number of the other elements of said at least one active phase.

DETAILED DESCRIPTION OF PREFERRED EMBODIMENTS OF THE INVENTION

More particularly according to the present invention, in a preferred embodiment thereof, in the at least one active phase having the formula (I), a is a whole or fractional number of up to 20 and more preferably ranges from 1 to 10, and b is a whole or fractional number of up to 20 and more preferably ranges from 0.1 to 10.

The active phase of the catalysts used in the process of the invention can also comprise, other than the elements of the formula (I), iron and/or gallium and/or indium.

Such active phase can thus be represented by the empirical formula (II):

$$V sb_a Bi_b M_c O_x \tag{II}$$

in which a is a whole or fractional number equal to or greater than 1, b is a whole or fractional number equal to or greater than 0.01, M is an iron and/or gallium and/or indium atom, c is a whole or fractional number equal to or greater than 0.1, and x is a whole or fractional number provided by the oxidation number of the other elements of the active phase.

In a preferred embodiment of the active phase having the formula (II), a is a whole or fractional number of up to 20, more preferably ranging from 1 to 10, b is a whole or fractional number of up to 20, more preferably ranging from 0.1 to 10, and c is a whole or fractional number of up to 20, preferably ranging from 0.5 to 10.

According to the present invention, acyclic saturated hydrocarbons having from 3 to 12 carbon atoms per molecule are reacted in the vapor phase with ammonia and oxygen in the presence of a catalyst, the active phase of which being as described above.

Of course, in the context of the process of the invention, it is possible to use diluent gases which are inert under the reaction conditions, such as helium, nitrogen and argon. Likewise, steam can be added to the gaseous reaction mixture over wide limits. The reactive gas (saturated hydrocarbon, ammonia, oxygen) can thus be diluted with an inert diluent and/or with steam. In this mixture, the content of steam can vary over wide limits, in particular from 0% to 50% and, preferably, from 3% to 30%. In another preferred embodiment of the invention, for good results the content of reactive gas will be at least 3% and preferably at least 20%.

Within the reactive gas, the respective contents of saturated hydrocarbon, ammonia and oxygen can also vary over wide limits.

The content of saturated hydrocarbon in the reactive gas preferably ranges from 5% to 70%. That of ammonia preferably ranges from 3% to 50% and that of oxygen preferably ranges from 3% to 45%.

Also for good results, the composition of the reactive mixture will be outside of the explosive region. Regarding the ammoxidation of propane in the absence of inert diluent, the composition (propane, oxygen, ammonia) will advantageously be selected from inside the quadrilateral ABDE which appears in the ternary diagram ABC shown in the accompanying FIG. 1.

Figure 1:
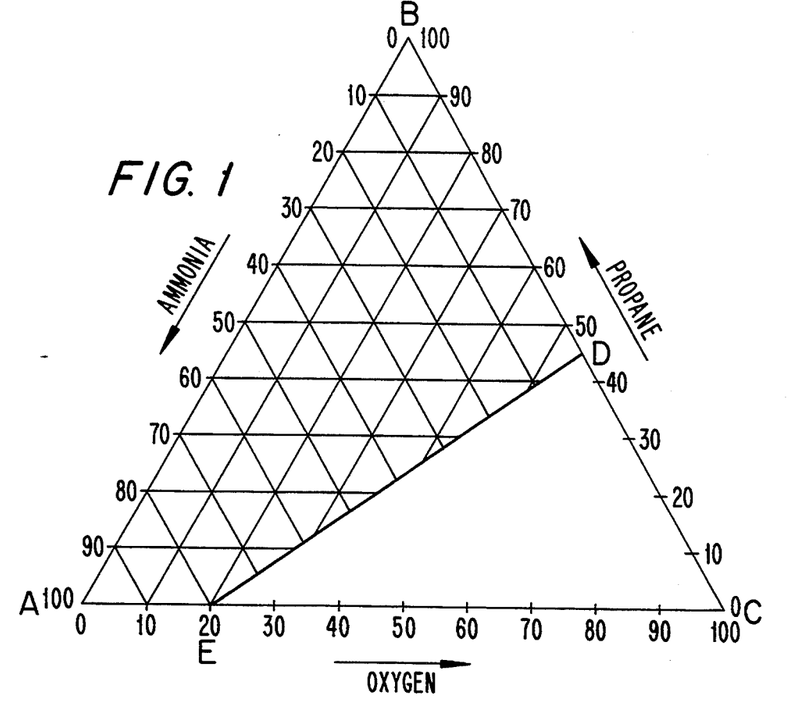
FIG. 1 is a ternary diagram indicating preferred compositions of certain gaseous feedstreams subjected to ammoxidation/conversion according to this invention.

In this ternary diagram, segment AB represents the ammonia content from 100% to 0%; segment BC represents the propane content from 100% to 0%; segment CA represents the oxygen content from 100% to 0%. Point D, situated on segment BC, corresponds to a propane content of 45% in the binary system (propane/$O_2$); point E, situated on segment AC, corresponds to an ammonia content of 79% in the binary system (ammonia/$O_2$).

Segment DE divides the ternary diagram into two parts: a triangle CDE within which is situated the explosive region (determined at 1 bar and at 25° C.) and a quadrilateral ABDE within which the composition of the reactive gaseous mixture will advantageously be selected.

Regarding the ammoxidation of propane in the presence of inert diluent gas(es) and/or of steam, it is advisable to determine the composition of the ternary mixture (propane, oxygen and ammonia) in order to situate it in the above-mentioned diagram, when the diluent gas and/or the steam is in low proportion.

Figure 2:
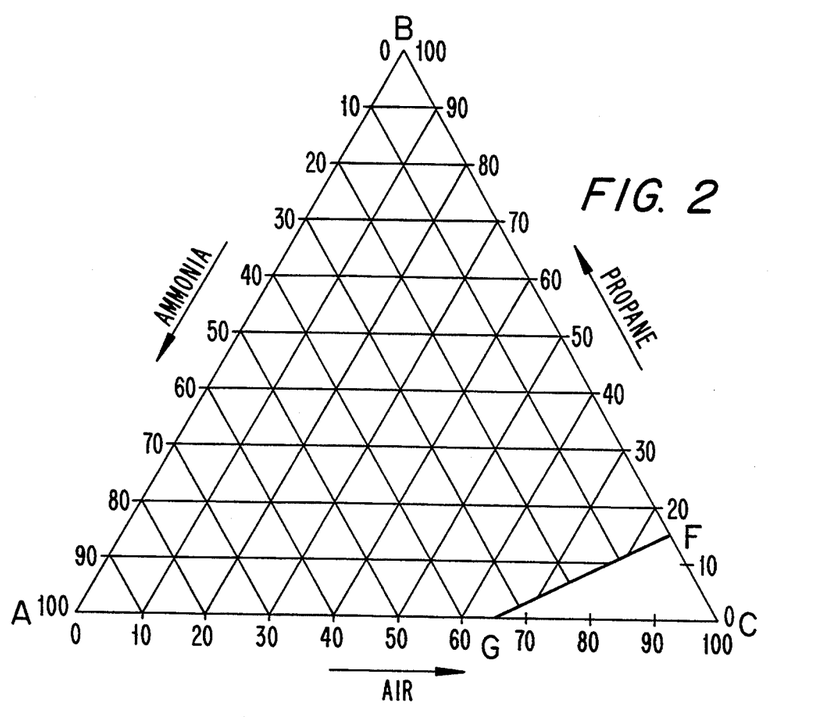
FIG. 2 is a ternary diagram indicating preferred compositions of certain other gaseous feedstreams subjected to ammoxidation/conversion according to the invention.

Regarding the ammoxidation of propane by means of air as the oxygen source, the composition (propane, air and ammonia) will advantageously be selected inside the quadrilateral ABFG which appears within diagram ABC shown in the accompanying FIG. 2.

In this second diagram, segment AB represents the ammonia content from 100% to 0%; segment BC represents the propane content from 100% to 0%; segment CA represents the air content from 100% to 0%. Point F, situated on segment BC, corresponds to a propane content of 16% in the binary system (propane/air); point G, situated on segment AC, corresponds to an ammonia content of 35% in the binary system (ammonia/air).

Segment FG divides the ternary diagram into two parts; a triangle CFG within which is situated the explosive region (determined at 1 bar and at 550° C.) and a quadrilateral ABFG within which the composition of the reactive gaseous mixture will advantageously be selected.

This second diagram will be used in the event that the oxygen/diluent gas mixture corresponds to an oxygen content equivalent to that of the air ($\approx 21\%$ oxygen) or in the event that this mixture is deficient in oxygen with respect to the air.

Starting from propane, a mixture will be obtained essentially consisting of propylene and acrylonitrile. Acrylonitrile is an intermediate produced industrially on a vast scale; propylene is a starting material traditionally used to produce acrylonitrile and various other intermediate compounds well known to this art.

Starting from isobutane, a mixture will be obtained containing methacrylonitrile and isobutene or n-butenes.

The process according to the invention is more particularly suitable for the ammoxidation of propane.

If the saturated hydrocarbon used can be of technical grade, it will not contain significant amounts of olefinically unsaturated compounds. Thus, the starting material propane will only contain trace amounts of propylene.

The process according to the invention is carried out as a vapor phase reaction. Consequently, any apparatus suitable for carrying out ammoxidation or oxidation reactions in the vapor phase can be used. The process can be carried out continuously or noncontinuously and it can comprise the use of a stationary bed or a fluidized bed.

The reaction temperature advantageously ranges from 300° C. to 550° C. and, preferably, from 400° C. to 500° C.

The total pressure of the reaction mixture can be greater than or equal to atmospheric pressure. It advantageously ranges from 1 to 6 bar and, preferably, from 1 to 4 bar.

The gas flow rate is advantageously fixed such that the hourly volume rate ranges from 100 to 36,000 $h^{-1}$ and, preferably, from 200 to 20,000 $h^{-1}$.

The hourly volume rate is defined as the ratio total gas volume/volume of the catalyst/hour.

Of course, those skilled in the art will be able to determine a compromise between the temperature, the gas flow rate, the precise nature of the catalyst used and the various other parameters of the reaction taking account of the production objectives.

In the process according to the invention, the catalysts can be prepared or used in the following manner:

An active phase comprising a mixed oxide containing the elements V, Sb and Bi and, if appropriate, the elements Fe and/or Ga and/or In, is first synthesized.

This active phase can optionally be deposited onto an inorganic oxide support or mixed with said inorganic oxide, per se known to this art, such as, for example, alumina, silica, silica/alumina, zirconia, cerite, magnesia, titanium dioxide or niobium oxide, utilizing various techniques also per se known to this art, such as impregnation or deposition by "slurry" technique.

The catalytic phase, namely, the active phase alone or the active phase deposited onto an inorganic oxide, or mixed with such inorganic oxide, can then be used in the bulk form or in the particulate state; it can thus be used in powder form or can be shaped into the form of, for example, beads, pellets, extrudates or crushed particles, according to various known techniques.

To carry out the process in a stationary bed, these techniques can be, for example, pelleting or coating on an inert support or on a ceramic or metal substrate of monolithic type.

To carry out the process in a moving bed or in a fluidized bed, the catalytic phase is generally formed by spraying, drying and calcination.

The catalytic phase thus formed, or in the powder form, constitutes the catalyst according to the invention.

When the catalytic phase comprises the active phase deposited onto an inorganic oxide or mixed with said inorganic oxide, one technique for the preparation thereof can entail, in a single stage, synthesizing the active phase and depositing it on to the inorganic oxide or mixing it with said inorganic oxide.

In the description that follows, the synthesis of the active phase and its deposition onto the inorganic oxide or its admixture with the inorganic oxide will be first described separately, but the description will also apply to the variation of synthesis of the active phase in the presence of the inorganic oxide.

The preparation of the active phases employed in the process according to the invention can be carried out by various known techniques, such as mixing of suitable salts or oxides of the various metals in water or in another solvent, followed by evaporation to dryness, or by precipitation by addition of a base such as aqueous ammonia or of an acid such as hydrochloric acid, or spraying of a suspension obtained after mixing the suitable salts.

The most commonly employed suitable salts contain anions or cations which can, for example, be decomposed by heat during the subsequent stages.

Exemplary such suitable salts or oxides of vanadium include ammonium vanadate, vanadium oxyhalides such as $VOCl_3$, $VOCl_2$, $(VO_2)Cl$, $VOCl$, $VOBr$, $VOBr_2$, $VOBr_3$, $VOF_3$ and $VOF_2$, vanadium halides such as $VF_3$, $VBr_3$ $VCl_2$, $VCl_3$, $VDl_4$, $VF_5$, $VF_4$, $VBr_2$ and $VI_2$, vanadyl sulfate, vanadyl acetylacetonate, meta-vanadic acid, hexacarbonylvanadium, vanadyl triisopropoxide, and vanadium oxides such as $V_2O_5$, $V_7O_{13}$, $VO$, $VO_2$, $V_2O_3$ and $V_3O_7$.

Exemplary suitable salts or oxides of antimony include antimony oxychloride, antimony halides such as $SbBr_3$, $SbCl_3$, $SbF_3$, $SbI_3$, $SbCl_5$, $SbF_5$ and $SbI_5$, antimony sulfate, antimony acetate, antimony tartrate, antimony ethoxide, antimony butoxide, the ethylene glycol derivative of antimony, antimony oxysulfate, or antimony oxides such as $Sb_2O_3$, $Sb_2O_4$ or $Sb_2O_5$.

Exemplary suitable salts or oxides of bismuth include bismuth nitrate, bismuth oxyhalides such as BiOCl, BiOI, BiOBr and BiOF, bismuth halides such as $BiCl_3$, $BiBr_3$, $BiF_3$, $BiI_3$, $BiCl_4$ and $BiI_2$, bismuth sulfate, bismuth acetate, bismuth propionate, bismuth oxalate, bismuth citrate, bismuth tartrate, bismuth lactate, bismuth benzoate, bismuth salicylate, bismuth oxycarbonate, bismuth oxynitrate, bismuth oxyperchlorate, or bismuth oxides such as $Bi_2O_3$ or $Bi_2O_5$.

Exemplary suitable salts or oxides of iron include iron nitrate, iron perchlorate, iron oxychloride, iron halides such as $FeCl_3$, $FeCl_2$, $FeBr_3$, $FeBr_2$, $FeF_3$, $FeF_2$ and $FeI_2$, iron phosphate, iron sulfate, iron iodate, pentacarbonyl-iron, iron acetate, iron acetylacetonate, iron citrate, iron formate, iron gluconate, iron glycerophosphate, iron lactate, iron malate, iron methoxide, iron oleate, iron oxalate, iron tartrate, iron 2-ethylhexanoate, or iron oxides such as $Fe_2O_3$, $Fe_3O_4$ or $FeO$.

Exemplary suitable salts or oxides of gallium include gallium nitrate, gallium perchlorate, gallium oxychloride, gallium halides such as $GaCl_3$, $GaCl_2$, $GaBr_3$, $GaF_3$ or $GaI_3$, gallium sulfate, gallium acetate, gallium acetylacetonate, gallium oxalate, or gallium oxides such as $Ga_2O_3$ or $Ga_2O$.

And exemplary suitable salts or oxides of indium include indium nitrate, indium perchlorate, indium halides such as $InCl_3$, $InCl_2$, $InCl$, $InBr_3$, $InBr_2$, $InBr$, $InF_3$, $InI_3$, $InI_2$ or $InI$, indium phosphate, indium sulfate, indium iodate, indium acetate, indium acetylacetonate, indium methoxide, or indium oxides such as $In_2O_3$, $In_2O$ or $InO$ The active phase is generally synthesized by the so-called evaporation method, in the following manner: an aqueous suspension of the suitable salts or oxides is prepared and the suspension is evaporated by heating to a temperature ranging from 20° to 100° C. until a viscous paste is obtained, which is dried. The precursor thus obtained can then be ground and calcined at a temperature of from 200° to 1,000° C. The active phase thus obtained can then, after cooling, be ground such that its particle size does not exceed approximately 400 $\mu m$.

The precursor can also be prepared by precipitation with addition, for example, of aqueous ammonia or of hydrochloric acid, during or at the end of mixing of the salts or oxides. It is preferable to heat the suspension at from 20° to 100° C. to drive the precipitation of the species to completion.

The suspension obtained can be evaporated under the conditions described above, or filtered and washed. The paste or filter cake, which are obtained, respectively, by evaporation or by filtration, are then dried, ground and calcined under the conditions described above in respect of the evaporation technique, to provide the active phase.

This active phase can optionally be deposited onto one or more inorganic oxides or can be mixed with the inorganic oxide(s) which are known to this art. Exemplary of the inorganic oxides suitable for the preparation of the catalysts of the invention are alumina, silica, silica/alumina, zirconia, cerite, magnesia, titanium dioxide or niobium oxide.

The deposition onto these oxides or the mixing with these inorganic oxides can be carried out by various known techniques, such as, for example, impregnation or "slurry" deposition.

The quantity of active phase, which can vary over wide limits, as a practical matter ranges from to 100% and preferably from 10% to 50% by weight with respect to the combined active phase+inorganic oxide.

Another such technique entails mixing of the inorganic oxide with the suitable salts or oxides of the various metals of the active phase under the conditions described above in respect of the preparation of the active phases. Once this mixture has been formulated, the precursor can be obtained by the so-called evaporation or precipitation methods, and then the paste or the filter cake thus produced are dried, ground and calcined under the conditions described above in respect of the preparation of the active phases.

The active phase, alone or deposited onto an inorganic oxide or mixed with an inorganic oxide such as those described above, constitutes the catalytic phase.

The catalytic phases can be used in the bulk form or in the particulate state. These phases can therefore be used in the powder form, or can be shaped for example, into the form of beads, pellets, extrudates or crushed particles, via any one of a number of known techniques.

To carry out the process in a stationary bed, exemplary techniques suitable for the preparation of the catalysts of the invention include pelleting or coating onto an inert support or onto a ceramic or metal substrate of monolithic type.

The catalytic phases according to the invention can, for example, be shaped by compression, to produce pellets. These pellets can then be optionally crushed into fragments. The precise values of the pressure, diameter and thickness of the pellets and particle size of the fragments easily be determined, depending upon the acceptable pressure drop in the reactor.

The catalytic phases according to the invention can also be deposited onto an inert support or can be coated thereon. The nature of this support is not critical as long as it is chemically inert with respect to the reactants under the reaction conditions selected. Exemplary supports suitable for the preparation of catalysts which can be used in the process of the invention include silica, alumina, silica/alumina, sintered clay, carborundum, magnesia, magnesium silicate and diatomaceous earth. This support is preferably nonporous and can, especially, be based on a refractory oxide in the particulate form, the most commonly employed support being clay-based. This support can, for example, comprise inert, complete, solid and rough clay beads having a diameter ranging from 0.5 mm to 6 mm. The precise value of the diameter of the beads can be selected as a function of the acceptable pressure drop in the reactor. This support can also be rendered nonporous, by enamelling.

Such support can also be a ceramic substrate, said substrate preferably being in the form of an inert and rigid structure of monolithic type comprising channels or ducts. Such supports are well known to this art and have been widely described in the literature. The substrates used which are shaped from ceramic materials are especially those containing, as the principal ingredient, cordierite, alumina, mullite, porcelain, and the carbides of boron or silicon.

This support can also be a metal substrate. Such supports are also well known to this art. Suitable metal substrates are especially those produced from alloys of iron, nickel and chromium, or those produced from alloys of iron, chromium, aluminum and cobalt, such as those marketed under the trademark Kanthal, or those produced from alloys of iron, chromium, aluminum and yttrium, marketed under the trademark Fecralloy. The metal can also be a carbon steel or simple cast iron.

When a coated catalyst is used, the amount of catalytic phase, which can vary over wide limits, typically ranges from 1% to 50% and preferably from 5% to 35% by weight with respect to the combined support-+catalytic phase.

Thus, certain catalysts, useful for carrying out the process in a stationary bed, can be prepared by coating ground, intermediate or finished, catalytic phases in a manner known per se. This conventional method entails depositing a layer of intermediate or finished catalytic phase around inert but rough beads. Once the beads are covered with the desired amount of the catalytic phase, they are dried with hot air at a temperature of from 70° to 150° C. for at least 30 minutes and then introduced into an oven to be calcined at from 300° to 600° C., preferably at from 450° to 500° C., for at least 3 hours.

Certain catalysts which are useful for carrying out the process according to the invention in a moving bed or fluidized bed can be produced by the technique, also known per se, of drying by spraying in a preferably nonreducing atmosphere. By such an operation, followed if appropriate by calcination at a temperature on the order of 400° to 1,100° C., powders are obtained which are spherical in shape and have a diameter ranging from 5 to 700 $\mu$m. Powders comprising at least 80% by weight of particles having sizes ranging from 5 to 200 $\mu$m are preferred when the subject process is carried out in a fluidized bed.

The catalytic phase thus employed in the bulk form or the particulate state constitutes the catalyst according to the invention.

The products of the reaction can be recovered from the effluent gases by any suitable means. For example, the effluent gases can be conveyed into a condenser containing dilute sulfuric acid in order to neutralize the unreacted ammonia. The gases can then pass through a refrigerated absorbing column to condense the acrylonitrile, acetonitrile and hydrocyanic acid, the uncondensed vapors principally containing unreacted propane, propylene, light hydrocarbons and, if appropriate, $CO_2$. The acrylonitrile and hydrocyanic acid can then be separated from the acetonitrile by distillation and the recovered acrylonitrile/hydrocyanic acid mixture can then in turn be distilled to separate the acrylonitrile from the hydrocyanic acid.

In order to further illustrate the present invention and the advantages thereof, the following specific examples are given, it being understood that same are intended only as illustrative and in nowise limitative.

EXAMPLE 1

Preparation of a Catalyst ($A_1$) According to the Invention Having the Empirical Formula (III):
$VSb_{3.5}Bi_2O_x/Al_2O_3$ (25/75% by weight) (III)

(A) A solution (a) of ammonium vanadate was prepared by dissolving 2.34 g of $NH_4VO_3$ in 400 cm$^3$ of demineralized water, a solution (b) of bismuth nitrate was prepared by dissolving 19.4 g of $Bi(NO_3)_3.5H_2O$ in 50 cm$^3$ of demineralized water and 15 cm$^3$ of concentrated nitric acid and a solution (c) of antimony chloride was prepared by dissolving 10.2 g of $Sb_2O_3$ in 250 cm$^3$ of 1N hydrochloric acid. Solution (b) was added to solution (a) with stirring at approximately 70° C. and then solution (c) was added. 47.3 g of $Al_2O_3$ were then added at approximately 90° C. The mixture was heated at 105° C. for 6 hours, evaporated to dryness, and the residue was dried at 120° C. for approximately 15 hours and then calcined at 550° C. for 10 hours.

(B) The product of formula (III) thus obtained was then compressed under a pressure of 4,300 kg/cm². Pellets were thus obtained having a diameter of 3 cm and a thickness of approximately 0.5 cm. These pellets were crushed into fragments having a particle size ranging from 0.3 to 0.8 cm constituting the catalyst $A_1$ in accordance with the invention.

EXAMPLE 2

Preparation of a Catalyst ($A_2$) According to the Invention Having the Empirical Formula: $VSb_{3.5}Bi_2O_x/Al_2O_3$ (25/75% by weight) coated on clay The product of formula (III) obtained in step (a) of Example 1 was then employed in the following manner:

15 g of said product prepared above were slowly dusted over 100 g of inert support composed of clay beads having a mean diameter of 4.8 mm, placed beforehand in a rotary coating device and moistened with 10% aqueous glucose solution; as soon as the beads were dry on the outside, a small amount of the glucose solution was sprayed thereon. The product of formula (III) was then again dusted onto the beads. These operations were continued alternately until all of the product of formula (III) had been coated thereon.

Drying was then carried out at 120° C. for 2 hours and calcination was carried out for 6 hours at 480° C.

The catalyst $A_2$ thus obtained consisted of 8.8% by weight of $VSb_{3.5}Bi_2O_x/Al_2O_3$ (25/75% by weight) coated onto clay beads.

EXAMPLE 3

Preparation of a Catalyst (B) According to Having the Empirical Formula (IV): $VSb_{1.64}Bi_{0.9}O_x$, coated onto clay beads A product of formula (IV) $VSb_{1.64}Bi_{0.9}O_x$ was prepared according to the following procedure:

A suspension of 19.3 g of $V_2O_5$ in 400 cm³ of demineralized water was prepared; 122.5 g of a 30% solution of $H_2O_2$ in water were added dropwise, with stirring, in three portions, respectively, of 49 g, 49 g and 24.5 g. A solution consisting of 92.7 g of $Bi(NO_3)_3.5H_2O$ in 24 cm³ of concentrated $HNO_3$ and 61 cm³ of demineralized water was then added. 50.8 g of $Sb_2O_3$ were then added. The mixture was heated to reflux, was allowed to evaporate to dryness, and the residue was dried at 120° C. for approximately 15 hours and then calcined at 650° C. for 8 hours.

The product of formula (IV) thus obtained had a specific surface, measured according to the B.E.T. method, of 11 m²/g.

9 g of the product of formula (IV) thus prepared were slowly dusted over 66 g of inert support composed of clay beads having a mean diameter of 4.8 mm, placed beforehand in a rotary coating device and moistened with 10% aqueous glucose solution. As soon as the beads were dry on the outside, a small amount of the glucose solution was sprayed thereon. The product of formula (IV) was then again dusted onto the beads. These operations were continued alternately until all of the said product had been coated onto the beads. Drying was then carried out at 120° C. for 2 hours and calcining at 480° C. for 6 hours.

The catalyst (B) thus obtained, in accordance with the invention, consisted of 12% by weight of $VSb_{1.64}Bi_{0.9}O_x$ coated onto clay beads.

EXAMPLE 4

Preparation of a Catalyst (G) According to the Invention Having the Empirical Formula (V): $VSb_{2.5}Bi_{0.5}O_x/Al_2O_3$ (50/50% by weight)

A product of formula (V) $VSb_{2.5}Bi0.5O_x$ was prepared according to the following procedure:

37.75 g of $Sb_2O_5$ were added with stirring to a hot solution of 10.92 g of ammonium vanadate in 300 cm³ of demineralized water. A solution of bismuth nitrate consisting of 22.6 g of $Bi(NO_3)_3.5H_2O$, 58 cm³ of demineralized water and 8.7 cm³ of 65% nitric acid was then added.

57 g of $Al_2O_3$ were then added. The mixture was evaporated to dryness, the product obtained was dried at 120° C. for approximately 15 hours, and then calcined at 290° C. for 3 hours, at 425° C. for 3 hours and at 610° C. for 3 hours.

The product obtained was then compressed under a pressure of 4,300 kg/cm². Pellets were thus obtained having a diameter of 3 cm and a thickness of approximately 0.5 cm. These pellets were then crushed into fragments having a particle size ranging from 0.3 cm to 0.8 cm.

The catalyst (G) thus obtained, in accordance with the invention, consisted of 50/50% by weight $VSb_{2.5}Bi$-$O0.5O_{x/Al2}O_3$.

EXAMPLE 5

Preparation of a Catalyst (H) According to the Invention Having the Empirical Formula (VI): $VSb_{3.5}Bi_2Fe_2O_x/Al_2O_3$ (25/75% by weight)

A product of formula (VI) $VSb3.5Bi_2Fe_2O_x$ was prepared according to the following procedure.

A solution of ammonium vanadate was prepared by dissolving 2 34 g of $NH_4VO_3$ in 350 cm³ of demineralized water. A solution of bismuth nitrate prepared by dissolving 19.4 g of $Bi(NO_3)_3.5H_2O$ in 50 cm³ of demineralized water and 15 cm³ of concentrated nitric acid was added with stirring and at approximately 70° C. and then a solution of iron nitrate, prepared by dissolving 16.2 g of $Fe(NO_3)_3.9H_2O$ in 70 cm³ of demineralized water, was added with stirring at approximately 70° C. A hot suspension of 10.2 g of $Sb_2O_3$ in 210 cm³ of demineralized water and 21 cm³ of concentrated hydrochloric acid was then added, and 47.3 g of alumina were then added when the mixture was at a temperature of approximately 95° C.

The mixture was heated to reflux for 6 hours and then evaporated to dryness, and the residue was dried at 120° C. for approximately 15 hours and calcined at 550° C. for approximately 10 hours.

The product obtained was then compressed under a pressure of 4,300 kg/cm². Pellets were thus obtained having a diameter of 3 cm and a thickness of approximately 0.5 cm. These pellets were then crushed into fragments having a particle size ranging from 0.3 cm to 0.8 cm.

The catalyst (H) thus obtained, in accordance with the invention, consisted of 25/75% by weight $VSb_{3.5}Bi_2Fe_2O_x/Al_2O_3$.

EXAMPLE 6

Preparation of a Catalyst (J) According to the Invention Having the Empirical Formula (VIII): $VSB_5Bi_2Fe_2O_x/Al_2O_3$ (25/75% by weight)

A product of formula (VII) $VSbSBi_2Fe_2O_x$ was prepared according to the following procedure:

A solution of ammonium vanadate was prepared by dissolving 2.34 g of $NH_4VO_3$ in 350 cm$^3$ of demineralized water. A solution of bismuth nitrate prepared by dissolving 19.4 g of $Bi(NO_3)_3.5H_2O$ in 50 cm$^3$ of demineralized water and 15 cm$^3$ of concentrated nitric acid was added with stirring and at approximately 70° C. and then a solution of iron nitrate, prepared by dissolving 16.2 g of $Fe(NO_3)_3.9H_2O$ in 70 cm$^3$ of demineralized water, was added with stirring at approximately 70° C. A hot suspension of 14.57 g of $Sb_2O_3$ in 300 cm$^3$ of demineralized water and 30 cm$^3$ of concentrated hydrochloric acid was then added, and 47.3 g of alumina were then added when the mixture was at a temperature of approximately 90° C.

The mixture was heated to reflux for 6 hours and then evaporated to dryness, and the residue was dried at 120° C. for approximately 15 hours and calcined at 550° C. for approximately 10 hours.

The product obtained was then compressed under a pressure of 4,300 kg/cm$^2$. Pellets were thus obtained having a diameter of 3 cm and a thickness of approximately 0.5 cm. These pellets were then crushed into fragments having a particle size ranging from 0.3 cm to 0.8 cm.

The catalyst (J) thus obtained, in accordance with the invention, consisted of 25/75% by weight $VSb_5Bi_2Fe_2O_x/Al_2O_3$.

EXAMPLE 7

Preparation of a Catalyst (K) According to the Invention Having the Empirical Formula (VIII): $VSb_5Bi_{0.5}Fe_5O_x/Al_2O_3$ (25/75% by weight)

A product of formula (VIII) $VSb_5Bi_{0.5}Fe_5O_x$ was prepared according to the following procedure.

A solution of ammonium vanadate was prepared by dissolving 2.34 g of $NH_4VO_3$ in 350 cm$^3$ of demineralized water. A solution of bismuth nitrate prepared by dissolving 4.85 g of $Bi(NO_3)_3.5H_2O$ in 20 cm$^3$ of demineralized water and 3.75 cm$^3$ of concentrated nitric acid was added with stirring and at approximately 70° C. and then a solution of iron nitrate, prepared by dissolving 40.5 g of $Fe(NO_3)_3.9H_2O$ in 100 cm$^3$ of demineralized water, was added with stirring at approximately 70° C. A hot suspension of 14.57 g of $Sb_2O_3$ in 300 cm$^3$ of demineralized water and 30 cm$^3$ of concentrated hydrochloric acid was then added, and 47.3 g of alumina were then added when the mixture was at a temperature of approximately 90° C.

The mixture was heated to reflux for 6 hours and then evaporated to dryness, and the residue was dried at 120° C. for approximately 15 hours and calcined at 550° C. for approximately 10 hours.

The product obtained was then compressed under a pressure of 4,300 kg/cm$^2$. Pellets were thus obtained having a diameter of 3 cm and a thickness of approximately 0.5 cm. These pellets were then crushed into fragments having a particle size ranging from 0.3 cam to 0. cm.

The catalyst (K) thus obtained, in accordance with the invention, consisted of 25/75% by weight $VSb_5Bi_{0.5}Fe_5O_x/Al_2O_3$.

EXAMPLE 8

Preparation of a Catalyst (L) According to the Invention Having the Empirical Formula (IX): $VSb_6Bi_6FeO_x/Al_2O_3$ (25/75% by weight)

A product of formula (IX) $VSb_6Bi_6FeO_x$ was prepared according to the following procedure:

A solution of ammonium vanadate was prepared by dissolving 2.34 g of $NH_4VO_3$ in 350 cm$^3$ of demineralized water. A solution of bismuth nitrate prepared by dissolving 58.2 g of $Bi(NO_3)_3.5H_2O$ in 120 cm$^3$ of demineralized water and 45 cm$^3$ of concentrated nitric acid was added with stirring and at approximately 70° C. and then a solution of iron nitrate, prepared by dissolving 8.1 g of $Fe(NO_3)_3.9H_2O$ in 20 cm$^3$ of demineralized water, was added with stirring at approximately 70° C. A hot suspension of 17.5 g of $Sb_2O_3$ in 180 cm$^3$ of demineralized water and 36 cm$^3$ of concentrated hydrochloric acid was then added, and 47.3 g of alumina were then added when the mixture was at a temperature of approximately 90° C.

The mixture was heated to reflux for 6 hours and then evaporated to dryness, and the residue was dried at 120° C. for approximately 15 hours and calcined at 550° C. for approximately 10 hours.

The product obtained was then compressed under a pressure of 4,300 kg/cm$^2$. Pellets were thus obtained having a diameter of 3 cm and a thickness of approximately 0.5 cm. These pellets were then crushed into fragments having a particle size ranging from 0.3 cm to 0.8 cm.

The catalyst (L) thus obtained, in accordance with the invention, consisted of 25/75% by weight $VSb_6Bi_6FeO_x/Al_2O_3$.

COMPARATIVE EXAMPLE 1

Preparation of a Catalyst (C) Not According to Intention, Having the Empirical Formula: $VSb_{1.64}O_x$, Coated Onto Clay Beads A product of composition $VSb_{1.64}Bi_{0.9}O_x$ was prepared according to the following procedure:

A suspension of 27.58 g of $V_2O_5$ in 400 cm$^3$ of demineralized water was prepared; 175 g of a 30% solution of $H_2O_2$ in water were added dropwise, with stirring, in three portions, respectively, of 70 g, 70 g and 35 g. 72.56 g of $Sb_2O_3$ and then 200 cm$^3$ of demineralized water were then added. The mixture was heated to reflux and permitted to evaporate to dryness. The product obtained was then dried at 120° C. for approximately 15 hours, and then calcined at 650° C. for 8 hours.

The product thus obtained had a specific surface, measured according to the B.E.T. method, of 55 m$^2$/g.

7.5 g of the product $VSb_{1.64}O_x$ thus obtained were slowly dusted over 50 g of inert support composed of clay beads having a mean diameter of 4.8 mm, placed beforehand in a rotary coating device and moistened with 10% aqueous glucose solution. As soon as the beads were dry on the outside, a small amount of the glucose solution was sprayed therein. The product $VSb_{1.64}O_x$ was then again dusted onto the beads. These operations were continued alternately until all of the said product had been coated thereon. Drying was then carried out at 120° C. for 2 hours and calcining at 480° C. for 6 hours.

The catalyst (C) thus obtained, not according to the invention, consisted of 10.55% by weight of $VSb_{1.64}O_x$ coated onto clay beads.

COMPARATIVE EXAMPLE 2

Preparation of a Catalyst (D) Not According to the Invention, Having the Empirical Formula: $VSb_{3.5}O_x/Al_2O_3$ (25/75% by weight)

A product having the composition $VSb_{3.5}O_x/Al_2O_3$ (25/75% by weight) was prepared according to the following procedure.

A solution (a) of ammonium vanadate was prepared by dissolving 2.34 g of $NH_4VO_3$ in 400 cm³ of demineralized water and a suspension (b) of antimony chloride was prepared by dissolving 10.2 g of $Sb_2O_3$ in 21 cm³ of hydrochloric acid and 230 cm³ of demineralized water. Suspension (b) was added to solution (a), and then 47.3 g of $Al_2O_3$ were added, with stirring at approximately 80°–90° C. The mixture was maintained at this temperature for 6 hours, was evaporated to dryness, and the residue was dried at 120° C. for approximately 15 hours and is then calcined at 550° C. for 10 hours.

This product was then compressed under a pressure of 4300 kg/cm². Pellets were thus obtained having a diameter of 3 cm and a thickness of approximately 0.5 cm. These pellets were then crushed into fragments having a particle size ranging from 0.3 cm to 0.8 cm, constituting the catalyst (D), of composition $VSb_{3.5}O_x/Al_2O_3$ (25/75% by weight), not according to the invention.

COMPARATIVE EXAMPLE 3

Preparation of a Catalyst (E) Not According to the Invention, Having the Empirical Formula: $BiV_{0.7}Sb_{0.5}O_x/SiO_2/Al_2I_3$ (50/25/25% by weight)

A product having the composition $BiV_{0.7}Sb_{0.5}O_x/SiO_2/Al_2O_3$ (50/25/25% by weight) was prepared according to the procedure described in U.S. Pat. No. 4,760,159:

10.78 g of $Sb_2O_5$ were added, with stirring, to a hot solution of ammonium vanadate (10.92 g of $NH_4VO_3$ in 300 cm³ of demineralized water). A solution of bismuth nitrate (64.7 g of $Bi(NO_3)_3.5H_2O$ in 150 cm³ of demineralized water and 25 cm³ of 65% nitric acid) was then added. 25 g of $Al_2O_3$ and 25 g of $SiO_2$ were then added. The mixture was permitted to evaporate to dryness, the product obtained was dried at 125° C. for approximately 15 hours, and was then calcined at 290° C. for 3 hours, at 425° C. for 3 hours and at 610° C. for 3 hours.

The product obtained was then compressed under a pressure of 4,300 kg/cm². Pellets were thus obtained having a diameter of 3 cm and a thickness of approximately 0.5 cm. These pellets were then crushed into fragments having a particle size ranging from 0.3 to 0.8 cm, constituting the catalyst (E), of composition $BiV_{0.7}Sb_{0.5}O_x/SiO_2/Al_2O_3$ (50/25/25% by weight), not according to the invention.

COMPARATIVE EXAMPLE 4

Preparation of a Catalyst (F) Not According to the Invention, Having the Empirical Formula: $BiV_{0.7}Sb_{0.5}O_x/Al_2O_3$ (50/50% by weight)

A product having the composition $BiV_{0.7}Sb_{0.5}O_x/Al_2O_3$ (50/50% by weight) was prepared according to the procedure described in U.S. Pat. No. 4,760,159:

10.78 g of $Sb_2O_5$ were added, with stirring, to a hot solution of ammonium vanadate (10.92 g of $NH_4VO_3$ in 300 cm³ of demineralized water). A solution of bismuth nitrate consisting of 64.7 g of $Bi(NO_3)_3.5H_2O$, 150 cm³ of demineralized water and 25 cm³ of 65% nitric acid was then added 50 g of $Al_2O_3$ were then added The mixture was permitted to evaporate to dryness, the product obtained was dried at 120° C. for approximately 15 hours, and was then calcined at 290° C. for 3 hours, at 425° C. for 3 hours and at 610° C. for 3 hours.

The product obtained was then compressed under a pressure of 4,300 kg/cm². Pellets were thus obtained having a diameter of 3 cm and a thickness of approximately 0.5 cm. These pellets were then crushed into fragments having a particle size ranging from 0.3 to 0.8 cm, constituting the catalyst (F), of composition $BiV_{0.7}Sb_{0.5}O_x/Al_2O_3$ (50/50% by weight), not according to the invention.

COMPARATIVE EXAMPLE 5

Preparation of a Catalyst (M) Not According to the Invention Having Empirical Formula: $VSb_{3.5}Fe_2O_x/Al_2O_3$ (25/75% by weight)

(A) A solution (a) of ammonium vanadate was prepared by dissolving 2.34 g of $NH_4VO_3$ in 400 cm³ of demineralized water, a solution (b) of iron nitrate was prepared by dissolving 16.2 g of $Fe(NO_3)_3.9H_2O$ in 70 cm³ of demineralized water and a suspension (c) of antimony chloride was prepared by dissolving 10.2 g of $Sb_2O_3$ in 250 cm³ of 1N hydrochloric acid. Solution (b) was added to solution (a) with stirring at approximately 70° C. and then suspension 9c) was added 47 3 g of $Al_2O_3$ were then added at approximately 90° C. The mixture was maintained at 90° C. for 6 hours, evaporated to dryness, and the residue was dried at 120° C. for approximately 15 hours and then calcined at 550° C. for 10 hours.

(B) The product thus obtained was then compressed under a pressure of 4300 kg/cm². Pellets were thus obtained having a diameter of 3 cm and a thickness of approximately 0.5 cm. These pellets were crushed into fragments having a particle size ranging from 0.3 to 0.8 cm constituting the catalyst M not according to the invention.

GENERAL PROCEDURE FOR THE AMMOXIDATION TESTS

The catalyst sample was heated beforehand to a temperature of 150° C. on a test bench while purging with helium for 10 min, and it was then subjected to a gas flow whose composition will be specified for each Example and which contained propane, ammonia, oxygen, steam and helium.

The total pressure of the reaction mixture, ranging from 1 to 6 bar, will also be specified for each Example.

The total gas flow rate was defined such as to provide an hourly volume rate (HVR) ranging from 100 to 36,000 $h^{-1}$, whose precise value will be indicated for each Example.

Catalyst volume: (catalytic phase + possible support): 25 cm³.

The principle of the ammoxidation test for propane was the following:

(i) The catalyst was heated to a temperature $T_1$, for example 300° C. and after stabilizing for 30 min at the temperature $T_1$, the composition of the mixture at the reactor outlet was determined by gas phase chromatography.

(ii) The conversion percentages and the selectivities obtained on the catalyst examined at the inlet temperature $T_1$ were calculated using relationships of the type:
  (1) Conversion of propane (% in moles) converted propane/introduced propane;
  (2) Selectivity for acrylonitrile (% in moles) = propane converted to acrylonitrile/converted propane.
(iii) The catalyst was then heated from 300° to 550° C. by increments of 20° C. and the conversion percentages and the selectivities were determined every 40 min.

In the Examples below, the following conventions are employed:
$DC(C_3H_8)$ = conversion of propane;
$S(ACN)$ = selectivity for acrylonitrile;
$S(ACN+C_3H_6)$ = selectivity towards acrylonitrile for propylene;
$S(CO_x)$ = selectivity for carbon monoxide and carbon dioxide;
$S(Ammox)$ = selectivity for acetonitrile, hydrocyanic acid and other (amm) oxidation byproducts;
$S(C_1-C_2)$ = selectivity for methane, ethane and ethylene.

EXAMPLE 9 AND COMPARATIVE EXAMPLE 6

Measurement of the performance of the catalysts $(A_1)$ and (E).

The operating conditions employed were the following:
Hourly volume rate = 1,000 h$^{-1}$
Total pressure = 1.3 bar
Composition by volume of the reaction mixture:
$C_3H_8 = 25\%$
$NH_3 = 25\%$
$O_2 = 10\%$
$H_2O = 20\%$
$He = 20\%$ The temperature conditions and the results obtained are reported in Table 1 below:

TABLE 1

| Tests Catalyst used | Example 9 $A_1$ | | | | Comparative Example 6 E | | | |
|---|---|---|---|---|---|---|---|---|
| Temperature (in °C.) | 400 | 420 | 440 | 460 | 400 | 420 | 440 | 460 |
| $DC(C_3H_8)$ % | 4 | 6 | 9 | 13 | 5 | 6 | 6 | 5 |
| $S(ACN)$ % | 37 | 49 | 60 | 67 | 22 | 27 | 27 | 19 |
| $S(ACN + C_3H_6)$ % | 58 | 70 | 77 | 79 | 65 | 66 | 68 | 66 |
| $S(Ammox)$ % | 42 | 30.5 | 23 | 21 | 35 | 31 | 27 | 29 |
| $S(C_1-C_2)$ % | 0 | 0 | 0 | 0 | 0 | 3 | 5 | 5 |
| $C(CO_x)$ % | 0 | 0 | 0 | 0 | 0 | 0 | 0 | 0 |

EXAMPLE 10 AND COMPARATIVE EXAMPLES 7 and 8

Measurement of the performance of the catalysts $(A_1)$, (D) and (E).

The operating conditions employed were the following:
Hourly volume rate = 1,000 h$^{-1}$
Total pressure = 1.3 bar
Composition by volume of the reaction mixture:
$C_3H_8 = 48\%$
$NH_3 = 9\%$
$O_2 = 18\%$
$H_2O = 20\%$
$He = 5\%$ The temperature conditions and the results obtained are reported in Table 2 below:

TABLE 2

| Tests Catalyst used | Example 10 $A_1$ | | | Comparative Example 7 D | | | Comparative Example 8 E | | |
|---|---|---|---|---|---|---|---|---|---|
| Temperature (in °C.) | 400 | 420 | 440 | 400 | 420 | 440 | 400 | 420 | 440 |
| $DC(C_3H_8)$ % | 5 | 10 | 14 | 18 | 17 | 19 | 9 | 9 | 11 |
| $S(ACN)$ % | 42 | 51 | 49 | 26 | 22 | 17 | 21 | 22 | 23 |
| $S(ACN + C_3H_6)$ % | 60 | 65 | 59 | 56 | 61 | 56 | 61 | 57 | 51 |
| $S(Ammox)$ % | 38 | 25 | 24 | 28 | 22 | 25 | 38 | 27 | 28 |
| $S(C_1-C_2)$ % | 0 | 1 | 3 | 1 | 0.3 | 3 | 1 | 3 | 4 |
| $S(CO_x)$ % | 1 | 9 | 15 | 15 | 17 | 17 | 0 | 13 | 18 |

EXAMPLE 11 AND COMPARATIVE EXAMPLE 9

Measurement of the performance of the catalysts $(A_1)$ and (E).

The operating conditions employed were the following:
Hourly volume rate = 1,000 h$^{-1}$
Total pressure = 1.3 bar
Composition by volume of the reaction mixture:
$C_3H_8 = 5.7\%$
$NH_3 = 15\%$
$O_2 = 15\%$
$H_2O = 20\%$
$He = 42.5\%$ The temperature conditions and the results obtained are reported in Table 3 below:

TABLE 3

| Tests Catalyst used | Example 11 $A_1$ | | | | | Comparative Example 9 E | | | |
|---|---|---|---|---|---|---|---|---|---|
| Temperature (in °C.) | 400 | 420 | 440 | 460 | 480 | 400 | 420 | 440 | 460 |
| $DC(C_3H_8)$ % | 1 | 5 | 10 | 19 | 30 | 12 | 21 | 28 | 32 |
| $S(ACN)$ % | 6 | 53 | 67 | 78 | 83 | 41 | 56 | 62 | 61 |
| $S(ACN + C_3H_6)$ % | 94 | 74 | 82 | 87 | 88 | 59 | 69 | 73 | 70 |
| $S(Ammox)$ % | 6 | 26 | 19 | 14 | 10 | 41 | 29 | 25 | 25 |
| $S(C_1-C_2)$ % | 0 | 0 | 0 | 0 | 0 | 0 | 1 | 2 | 4 |

TABLE 3-continued

| Tests | Example 11 | | | | | Comparative Example 9 | | | |
|---|---|---|---|---|---|---|---|---|---|
| Catalyst used | $A_1$ | | | | | E | | | |
| Temperature (in °C.) | 400 | 420 | 440 | 460 | 480 | 400 | 420 | 440 | 460 |
| $S(CO_x)$ % | 0 | 0 | 0 | 0 | 1 | 0 | 0 | 0 | 0 |

EXAMPLE 12 AND COMPARATIVE EXAMPLE 10

Measurement of the performance of the catalysts (B) and (C).

The operating conditions employed were the following:
Hourly volume rate = 1,000 h$^{-1}$
Total pressure = 1.3 bar
Composition by volume of the reaction mixture:
$C_3H_8 = 25$ %
$NH_3 = 10$%
$O = 25$%
$H_2O = 20$%
$He = 20$%

The temperature conditions and the results obtained are reported in Table 4 below:

TABLE 4

| Tests | Example 12 | | Comparative Example 10 | |
|---|---|---|---|---|
| Catalyst used | B | | C | |
| Temperature (in °C.) | 460 | 480 | 460 | 480 |
| $DC(C_3H_8)$ % | 10 | 14 | 36 | 36 |
| $S(ACN)$ % | 45 | 40 | 48 | 23 |
| $S(ACN + C_3H_6)$ % | 73 | 67 | 54 | 61 |
| $S(Ammox)$ % | 23 | 22 | 36 | 23 |
| $S(C_1-C_2)$ % | 2 | 3 | 1 | 1 |
| $S(CO_x)$ % | 2 | 8 | 9 | 14 |

EXAMPLE 13 AND COMPARATIVE EXAMPLE 11

Measurement of the performance of the catalysts (B) and (C).

The operating conditions employed were the following:
Hourly volume rate = 1,000 h$^{-1}$
Total pressure = 1.3 bar
Composition by volume of the reaction mixture:
$C_3H_8 = 7.5$%
$NH_3 = 15$%
$O_2 = 15$%
$H_2O = 20$%
$He = 42.5$%

The temperature conditions and the results obtained are reported in Table 4 below:

TABLE 5

| Tests | Example 13 | | Comparative Example 11 | |
|---|---|---|---|---|
| Catalyst used | B | | C | |
| Temperature (in °C.) | 460 | 480 | 460 | 480 |
| $DC(C_3H_8)$ % | 11 | 14 | 23 | 28 |
| $S(ACN)$ % | 46 | 53 | 38 | 47 |
| $S(ACN + C_3H_6)$ % | 71 | 77 | 48 | 55 |
| $S(Ammox)$ % | 24 | 21 | 49 | 42 |
| $S(C_1-C_2)$ % | 5 | 2 | 1 | 4 |
| $S(CO_x)$ % | 0 | 0 | 2 | 0 |

EXAMPLE 14

Measurement of the performance of the catalyst ($A_2$).

The operating conditions employed were the following:
Hourly volume rate = 1,000 h$^{-1}$
Total pressure = 1.3 bar
Composition by volume of the reaction mixture:
$C_3H_8 = 48$%
$NH_3 = 9$%
$O_2 = 18$%
$H_2O = 20$%
$He = 5$%

The temperature conditions and the results obtained are reported in Table 6 below:

TABLE 6

| | 460° C. | 480° C. |
|---|---|---|
| $DC(C_3H_8)$ % | 2% | 3.5% |
| $S(ACN)$ % | 17% | 12% |
| $S(ACN + C_3H_6)$ % | 65% | 65% |
| $S(Ammox)$ % | 33% | 27% |
| $S(C_1-C_2)$ % | 2% | 8% |
| $S(CO_x)$ % | 0% | 0% |

EXAMPLE 15 AND COMPARATIVE EXAMPLE 12

Measurement of the performance of the catalysts (G) and (F).

The operating conditions employed were the following:
Hourly volume rate = 1,000 h$^{-1}$
Total pressure = 1.3 bar
Composition by volume of the reaction mixture:
$C_3H_8 = 7.5$%
$NH_3 = 15$%
$O_2 = 15$%
$H_2O = 20$%
$He = 42.5$%

The temperature conditions and the results obtained are reported in Table 7 below:

TABLE 7

| Tests | Example 15 | | | | Comparative Example 12 | | | |
|---|---|---|---|---|---|---|---|---|
| Catalyst used | G | | | | F | | | |
| Temperature (in °C.) | 360 | 380 | 400 | 440 | 360 | 380 | 400 | 440 |
| $DC(C_3H_8)$ % | 6 | 18 | 33 | 51 | 3 | 6 | 14 | 30 |
| $S(ACN)$ % | 13 | 32 | 38 | 53 | 3 | 5 | 8 | 8 |
| $S(ACN + C_3H_6)$ % | 46 | 46 | 47 | 60 | 15 | 14 | 13 | 10 |
| $S(Ammox)$ % | 50 | 45 | 33 | 26 | 85 | 85 | 87 | 88 |
| $S(C_1-C_2)$ % | 0 | 0 | 0 | 0 | 0 | 0 | 0 | 2 |
| $S(CO_x)$ % | 4 | 8 | 20 | 13 | 0 | 0 | 0 | 0 |

EXAMPLE 16

Measurement of the performance of the catalyst (G).

The operating conditions employed were the following:
Hourly volume rate = 1,000 h$^{-1}$
Total pressure = 1.3 bar
Composition by volume of the reaction mixture:
$C_3H_8 = 20$%
$NH_3 = 20$%

$O_2 = 20\%$
$H_2O = 20\%$
$He = 20\%$

The temperature conditions and the results obtained are reported in Table 8 below:

TABLE 8

|  | 360° C. | 380° C. | 400° C. | 420° C. |
|---|---|---|---|---|
| DC($C_3H_8$) % | 23% | 26% | 26% | 26% |
| S(ACN) % | 34% | 32% | 25% | 26% |
| S(ACN + $C_3H_6$) % | 51% | 52% | 49% | 51% |
| S(Ammox) % | 36% | 36% | 37% | 34% |
| S($C_1$-$C_2$) % | 0.1% | 0.3% | 0.2% | 0% |
| S($CO_x$) % | 13% | 12% | 14% | 15% |

EXAMPLE 17 AND COMPARATIVE EXAMPLE 13

Measurement of the performance of the catalysts (H) and (M).

The operating conditions employed were the following:
Hourly volume rate 1,000 h$^{-1}$
Total pressure = 1.3 bar
Composition by volume of the reaction mixture:
$C_3H_8 = 7.5\%$
$NH_3 = 15\%$
$O_2 = 15\%$
$H_2O = 20\%$
$He = 42.5\%$ The temperature conditions and the results obtained are reported in Table 9 below:

TABLE 9

| Tests | Example 17 | | | | | Comparative Example 13 | | | |
|---|---|---|---|---|---|---|---|---|---|
| Catalyst used | H | | | | | M | | | |
| Temperature (in °C.) | 380 | 400 | 420 | 440 | 460 | 400 | 420 | 440 | 460 |
| DC($C_3H_8$) % | 3 | 7 | 16 | 21 | 23 | 5 | 15 | 31 | 38 |
| S(ACN) % | 47 | 73 | 85 | 90 | 81 | 34 | 66 | 74 | 66 |
| S(ACN + $C_3H_6$) % | 68 | 84 | 89 | 93 | 83 | 65 | 78 | 81 | 75 |
| S(Ammox) % | 32 | 16 | 11 | 6 | 7 | 33 | 18 | 18 | 10 |
| S($C_1$-$C_2$) % | 0 | 0 | 0 | 0 | 10 | 0 | 4 | 0 | 0 |
| S($CO_x$) % | 0 | 0 | 0 | 0 | 0 | 2 | 0 | 0 | 16 |

EXAMPLE 18 AND COMPARATIVE EXAMPLE 14

Measurement of the performance of the catalysts (H) and (M).

The operating conditions employed were the following:
Hourly volume rate = 1,000 h$^{-1}$
Total pressure = 1.3 bar
Composition by volume of the reaction mixture:
$C_3H_8 = 48\%$
$NH_3 = 9\%$
$O_2 = 18\%$
$H_2O = 20\%$
$He = 5\%$ The temperature conditions and the results obtained are reported in Table 10 below:

TABLE 10

| Tests | Example 18 | | | Comparative Example 14 | | |
|---|---|---|---|---|---|---|
| Catalyst used | H | | | M | | |
| Temperature (in °C.) | 360 | 380 | 400 | 360 | 380 | 400 |
| DC($C_3H_8$) % | 3 | 6 | 10 | 4 | 10 | 12 |
| S(ACN) % | 20 | 47 | 47 | 10 | 34 | 36 |
| S(ACN + $C_3H_6$) % | 37 | 63 | 58 | 43 | 60 | 63 |
| S(Ammox) % | 63 | 37 | 30 | 56 | 39 | 36 |
| S($C_1$-$C_2$) % | 0 | 0 | 1 | 0 | 0 | 0 |
| S($CO_x$) % | 0 | 0 | 10 | 0 | 0 | 0 |

EXAMPLE 19

Measurement of the performance of the catalyst (J).

The operating conditions employed were the following:
Hourly volume rate = 1,000 h$^{-1}$
Total pressure = 1.3 bar
Composition by volume of the reaction mixture:
$C_3H_8 = 7.5\%$
$NH_3 = 15\%$
$O_2 = 15\%$
$H_2O = 20\%$
$He = 42.5\%$ The temperature conditions and the results obtained are reported in Table 11 below:

TABLE 11

| Temperature (in °C.) | 380 | 400 | 420 | 440 | 460 |
|---|---|---|---|---|---|
| DC($C_3H_8$) % | 3 | 7 | 14 | 22 | 39 |
| S(ACN) % | 23 | 48 | 80 | 89 | 82 |
| S(ACN + $C_3H_6$) % | 38 | 55 | 85 | 92 | 84 |
| S(Ammox) % | 62 | 45 | 15 | 8 | 16 |
| S($C_1$-$C_2$) (%) | 0 | 0 | 0 | 0 | 0 |
| S($CO_x$) % | 0 | 0 | 0 | 0 | 0 |

EXAMPLES 20 AND 21

Measurement of the performance of the catalyst (J).
The operating conditions employed were the following:
Hourly volume rate = 1,000 h$^{-1}$
Total pressure = 1.3 bar
Composition by volume of the reaction mixture:

EXAMPLE 20

$C_3H_8 = 20\%$
$NH_3 = 20\%$
$O_2 = 20\%$
$H_2O = 20\%$
$He = 20\%$

EXAMPLE 21

$C_3H_8 = 48\%$
$NH_3 = 9\%$
$O_2 = 18\%$
$H_2O = 20\%$
$He = 5\%$

The temperature conditions and the results obtained are reported in Table 12 below:

TABLE 12

| Temperature (in °C.) | Example 20 | | | Example 21 | |
|---|---|---|---|---|---|
| | 380 | 400 | 420 | 380 | 400 |
| DC($C_3H_8$) % | 3 | 5 | 9 | 9 | 9 |
| S(ACN) % | 30 | 56 | 52 | 31 | 32 |
| S(ACN + $C_3H_6$) % | 41 | 65 | 59 | 42 | 44 |
| S(Ammox) % | 54 | 35 | 41 | 58 | 26 |
| S($C_1$-$C_2$) (%) | 5 | 0 | 0 | 0 | 1 |
| S($CO_x$) % | 0 | 0 | 0 | 0 | 28 |

EXAMPLE 22

Measurement of the performance of the catalyst (K).
The operating conditions employed were the following:
Hourly volume rate = 1,000 h$^{-1}$
Total pressure = 1.3 bar
Composition by volume of the reaction mixture:
$C_3H_8$ = 7.5%
$NH_3$ = 15%
$O_2$ = 15%
$H_2O$ = 20%
He = 42.5%

The temperature conditions and the results obtained are reported in Table 13 below:

TABLE 13

| Temperature (in °C.) | 360 | 380 | 400 | 420 | 440 | 460 |
|---|---|---|---|---|---|---|
| DC($C_3H_8$) % | 4 | 11 | 18 | 29 | 39 | 40 |
| S(ACN) % | 31 | 56 | 75 | 84 | 77 | 71 |
| S(ACN + $C_3H_6$) % | 43 | 61 | 80 | 87 | 80 | 74 |
| S(Ammox) % | 57 | 39 | 20 | 10 | 14 | 21 |
| S($C_1$-$C_2$) (%) | 0 | 0 | 0 | 0 | 0 | 1 |
| S($CO_x$) % | 0 | 0 | 0 | 3 | 6 | 4 |

EXAMPLE 23

Measurement of the performance of the catalyst (K).
The operating conditions employed were the following:
Hourly volume rate = 1,000 h$^{-1}$
Total pressure = 1.3 bar
Composition by volume of the reaction mixture:
$C_3H_8$ = 20%
$NH_3$ = 20%
$O_2$ = 20%
$H_2O$ = 20%
He = 20%

The temperature conditions and the results obtained are reported in Table 14 below:

TABLE 14

| Temperature (in °C.) | 360 | 380 | 400 | 410 |
|---|---|---|---|---|
| DC($C_3H_8$) % | 3 | 7 | 21 | 23 |
| S(ACN) % | 25 | 53 | 54 | 57 |
| S(ACN + $C_3H_6$) % | 39 | 65 | 60 | 65 |
| S(Ammox) % | 61 | 35 | 40 | 35 |
| S($C_1$-$C_2$) (%) | 0 | 0 | 0 | 0 |
| S($CO_x$) % | 0 | 0 | 0 | 0 |

EXAMPLE 24

Measurement of the performance of the catalyst (K).
The operating conditions employed were the following:
Hourly volume rate = 1,000 h$^{-1}$
Total pressure = 1.3 bar
Composition by volume of the reaction mixture:
$C_3H_8$ = 48%
$NH_3$ = 9%
$O_2$ = 18%
$H_2O$ = 20%
He = 5%

The temperature conditions and the results obtained are reported in Table 15 below:

TABLE 15

| Temperature (in °C.) | 360 | 380 | 390 | 400 | 410 |
|---|---|---|---|---|---|
| DC($C_3H_8$) % | 6 | 9 | 11 | 12 | 12 |
| S(ACN) % | 19 | 28 | 32 | 42 | 46 |
| S(ACN + $C_3H_6$) % | 37 | 49 | 48 | 56 | 60 |
| S(Ammox) % | 63 | 51 | 40 | 28 | 24 |
| S($C_1$-$C_2$) (%) | 0 | 0 | 0 | 1 | 0 |
| S($CO_x$) % | 0 | 0 | 12 | 15 | 16 |

EXAMPLE 25

Measurement of the performance of the catalyst (L).
The operating conditions employed were the following:
Hourly volume rate = 1,000 h$^{-1}$
Total pressure = 1.3 bar
Composition by volume of the reaction mixture:
$C_3H_8$ = 7.5%
$NH_3$ = 15%
$O_2$ = 15%
$H_2O$ = 20%
He = 42.5%

The temperature conditions and the results obtained are reported in Table 16 below:

TABLE 16

| Temperature (in °C.) | 380 | 400 | 420 | 440 | 460 | 470 |
|---|---|---|---|---|---|---|
| DC($C_3H_8$) % | 1 | 3 | 5 | 7 | 16 | 29 |
| S(ACN) % | 18 | 33 | 53 | 70 | 84 | 90 |
| S(ACN + $C_3H_6$) % | 18 | 42 | 61 | 76 | 86 | 91 |
| S(Ammox) % | 82 | 58 | 39 | 24 | 14 | 7 |
| S($C_1$-$C_2$) (%) | 0 | 0 | 0 | 0 | 0 | 2 |
| S($CO_x$) % | 0 | 0 | 0 | 0 | 0 | 0 |

Measurement of the performance of the catalyst (L).
The operating conditions employed were the following:
Hourly volume rate = 1,000 h$^{-1}$
Total pressure = 1.3 bar
Composition by volume of the reaction mixture:
$C_3H_8$ = 20%
$NH_3$ = 20%
$O_2$ = 20%
$H_2O$ = 20%
He = 20%

The temperature conditions and the results obtained are reported in Table 17 below:

TABLE 17

| Temperature (in °C.) | 380 | 300 | 420 | 440 |
|---|---|---|---|---|
| DC($C_3H_8$) % | 2 | 4 | 8 | 13 |
| S(ACN) % | 14 | 28 | 50 | 72 |
| S(ACN + $C_3H_6$) % | 17 | 31 | 53 | 74 |
| S(Ammox) % | 83 | 69 | 47 | 26 |
| S($C_1$-$C_2$) (%) | 0 | 0 | 0 | 0 |
| S($CO_x$) % | 0 | 0 | 0 | 0 |

EXAMPLE 27

Measurement of the performance of the catalyst (L).
The operating conditions employed were the following:
Hourly volume rate = 1,000 h$^{-1}$ Total pressure=1.3 bar
Composition by volume of the reaction mixture:
C₃H₈=48%
NH₃=9%
O₂=18%
H₂O=20%
He=5%

The temperature conditions and the results obtained are reported in Table 18 below:

TABLE 18

| Temperature (in °C.) | 380 | 400 | 420 |
|---|---|---|---|
| DC(C₃H₈) % | 3 | 5 | 11 |
| S(ACN) % | 18 | 40 | 68 |
| S(ACN + C₃H₆) % | 25 | 47 | 73 |
| S(Ammox) % | 75 | 53 | 26 |
| S(C₁-C₂) (%) | 0 | 0 | 1 |
| S(CO$_x$) % | 0 | 0 | 0 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the ammoxidation of an alkane into an α,β-ethylenically unsaturated nitrile, by reacting an acyclic alkane containing at least 3 carbon atoms per molecule with ammonia and oxygen, in vapor phase, and in the presence of a catalytically effective amount of a solid catalyst, said catalyst having a single active phase represented by the empirical formula (I):

$$VSb_aBi_bO_x \qquad (I)$$

in which a is a number equal to or greater than 1, b is a number equal to or greater than 0.01, and x is a number provided by the oxidation number of the other elements of said active catalytic phase, and said active catalytic phase represented by formula (I) being the sole ammoxidation catalytic component in the process.

2. A process for the ammoxidation of an alkane into an α,β-ethylenically unsaturated nitrile, by reacting an acyclic alkane containing at least 3 carbon atoms per molecule with ammonia and oxygen, in vapor phase, and in the presence of a catalytically effective amount of a solid catalyst having a single active phase represented by the empirical formula (II):

$$VSb_aBi_bM_cO_x \qquad (II)$$

in which a is a number equal to or greater than 1; b is a number equal to or greater than 0.01; M is iron, gallium, indium or mixtures thereof; c is a number equal to or greater than 0.1, and x is a number provided by the oxidation number of the other elements of said active catalytic phase, and said active catalytic phase represented by formula (I) being the sole ammoxidation catalytic component in the process.

3. The process as defined by claim 1, wherein said at least one active catalytic phase having the formula (I), a is a whole or fractional number ranging from 1 to 20, and b is a whole or fractional number ranging from 0.01 to 20.

4. The process as defined by claim 3, wherein said at least one active catalytic phase having the formula (I), a is a whole or fractional number ranging from 1 to 10, and b is a whole or fractional number ranging from 0.01 to 10.

5. The process as defined by claim 2, wherein said at least one active catalytic phase having the formula (II), a is a whole or fractional number ranging form 1 to 20, b is a whole or fractional number ranging from 0.01 to 20, and c is a whole or fractional number ranging from 0.1 to 20.

6. The process as defined by claim 5, wherein said at least one active catalytic phase having the formula (II), a is a whole or fractional number ranging from 1 to 10 b is a whole or fractional number ranging from 0.01 to 10, and c is a whole or fractional number ranging from 0.5 to 10.

7. The process as defined by claims 1 or 2, carried out at a temperature ranging from 300° to 550° C.

8. The process as defined by claim 7, carried out at a temperature ranging from 400° to 500° C.

9. The process as defined by claim 7, said alkane reactant comprising propane.

10. The process as defined by claim 7, carried out under a total pressure ranging from 1 to 6 bar.

11. The process as defined by claim 7, carried out at an hourly volume rate ranging from 100 to 36,000 h⁻¹.

12. The process as defined by claim 7, the gaseous mixture of reaction comprising from 5% to 70% of said alkane, from 3% to 50% of ammonia, and from 3% to 45% of oxygen.

13. The process as defined by claim 7, the composition of the gaseous mixture of reaction being outside the explosive region thereof.

14. The process as defined by claim 7, said solid catalyst further comprising at least one inorganic oxide has an inert support.

15. The process as defined by claim 14, said at least one inorganic oxide comprising alumina, silica, silica/alumina, zirconia, cerite, magnesia, titanium dioxide, niobium oxide, or mixture thereof.

16. The process as defined by claim 7, said solid catalyst further comprising a ceramic or metal substrate.

17. The process as defined by claim 14, said at least one active catalytic phase comprising at least by weight of said solid catalyst.

18. The process as defined by claim 7, said at least one active catalytic phase comprising from 1% to 50% by weight of said solid catalyst.

19. The process as defined by claim 16, said at least one active catalytic phase comprising from 1% to 50% by weight of said solid catalyst.

20. The process as defined by claim 17, said at least one active catalytic phase comprising from 10% to 50% by weight of said solid catalyst.

21. The process as defined by claim 7, carried out in the presence of steam or an inert diluent.

* * * * *